US012766095B2

(12) United States Patent
Faber

(10) Patent No.: US 12,766,095 B2
(45) Date of Patent: Oct. 20, 2026

(54) COMPOSITIONS FOR NASAL APPLICATION

(71) Applicant: Patrick Faber, Vienna (AT)

(72) Inventor: Patrick Faber, Vienna (AT)

( * ) Notice: Subject to any disclaimer, the term of this patent is extended or adjusted under 35 U.S.C. 154(b) by 552 days.

(21) Appl. No.: 18/251,018

(22) PCT Filed: Nov. 3, 2021

(86) PCT No.: PCT/EP2021/080455
§ 371 (c)(1),
(2) Date: Apr. 28, 2023

(87) PCT Pub. No.: WO2022/096481
PCT Pub. Date: May 12, 2022

(65) Prior Publication Data

US 2024/0342079 A1 Oct. 17, 2024

(30) Foreign Application Priority Data

Nov. 3, 2020 (EP) ..................................... 20205430

(51) Int. Cl.
*A61K 9/00* (2006.01)
*A61K 31/198* (2006.01)
*A61K 31/405* (2006.01)
*A61K 31/522* (2006.01)

(52) U.S. Cl.
CPC .......... *A61K 9/0043* (2013.01); *A61K 31/198* (2013.01); *A61K 31/405* (2013.01); *A61K 31/522* (2013.01)

(58) Field of Classification Search
None
See application file for complete search history.

(56) References Cited

U.S. PATENT DOCUMENTS 4,778,810 A * 10/1988 Wenig .................. A61K 9/0043 514/263.34
2004/0092470 A1 5/2004 Leonard et al.
2005/0019411 A1 1/2005 Colombo et al.
2014/0242067 A1* 8/2014 Frey, II .................. C07K 16/18 424/130.1

FOREIGN PATENT DOCUMENTS

DE 102011114094 A1 3/2013
WO 2006084894 A2 8/2006

OTHER PUBLICATIONS

"Rosy Lemonade Flavou Intra-workou Food Supplement Powder" 2019.*
Eskelinen et al. "Caffeine as a protective factor in dementia and Alzheimer's disease." 2010.*
Frank et al. "Effects of Anatomy and Particle Size on Nasal Sprays and Nebulizers" 2011.*
Montagne "Drug-Taking Paraphernalia" 1983.*
European Search Report received in Application No. 20205430.0 dated Apr. 12, 2021.
International Search Report and Written Opinion received for PCT/EP2021/080455, mailed Jan. 11, 2022.
Dunst, B., et al., "Neural efficiency as a function of task demands," Intelligence 42, 2014, pp. 22-30.
Grabner, R., et al., "When intelligence loses its impact: neural efficiency during reasoning in a familiar area," International Journal of Psychophysiology 49, 2003, pp. 89-98.
Mintel, "GSC Products: Energy Nasal Spray," Product Description, Database GNPD, retrieved from http://www.gnpd.com, Mar. 8, 2012, 3 pages.
Mintel, "Prozis: Rosy Lemonde Flavour Intra-Workout Food Supplement Powder," Product Description, Database GNPD, retrieved from http://www.gnpd.com, Oct. 21, 2019, 3 pages.
Neubauer, A., et al., "Intelligence and neural efficiency," Neuroscience & Biobehavioral Reviews, vol. 33, Issue 7, Jul. 2009, pp. 1004-1023.

* cited by examiner

*Primary Examiner* — Danah Al-Awadi
(74) *Attorney, Agent, or Firm* — Greer, Burns & Crain, Ltd

(57) ABSTRACT

Pulverulent compositions for a nasal application containing taurine, caffeine, L-arginine and L-tryptophan, and containers and kits containing such compositions, and to uses of the compositions are discussed.

4 Claims, No Drawings

COMPOSITIONS FOR NASAL APPLICATION

BACKGROUND

The field of the present invention is compositions containing taurine and caffeine and uses thereof.

Ingestible compositions containing caffeine and/or taurine are known from the prior art. These are often drink preparations, for example "energy drinks", which may additionally contain vitamins, sugar or sweeteners. Taking such energy drinks can have a temporary performance-enhancing effect.

For example, WO 2006/084894 A2 discloses foods and beverages containing caffeine, taurine and tryptophan. The administration of tryptophan together with caffeine and taurine is said to lead to a significant improvement in cognitive performance by increasing neural efficiency.

DE 10 2011 114094 A1 discloses compositions containing an essential oil and a stimulating substance, for example caffeine and/or taurine for nasal and/or inhalative application, for example as a nasal spray. Tryptophan is not mentioned.

US 2005/019411 A1 relates to powder formulations for nasal administration. Caffeine is mentioned as one of many possible active ingredients. Amino acids are generally mentioned as possible excipients. However, the document does not mention the amino acid tryptophan, nor taurine.

US 2004/092470 A1 relates to dry powder formulations containing oligonucleotides, in particular DNA or RNA. The formulations can be administered nasally. As excipients which may be contained in the formulations, amino acids are mentioned among a number of other possibilities. Caffeine is only mentioned as a possible modified nucleobase; taurine is not mentioned at all.

The nasal spray "Energy Nasal Spray-Turbo Snort" (MINTEL GNPD [Online], "Energy Nasal Spray", Database accession no. 1752088, 8 Mar. 2012) contains an aqueous solution with taurine, caffeine, creatine, glutamine and vitamin C.

The preparation "Prozis Big Shot" (MINTEL GNPD [Online], "Rosy Lemonade Flavour Intra-Workout Food Supplement Powder", Database accession no. 6969675, 21 Oct. 2019) is an instant drink powder containing, among other things, taurine, caffeine, and L-tryptophan.

Despite numerous compositions known from the prior art, there is still a need for improved compositions containing taurine and/or caffeine. In particular, there is a need for compositions that have an improved effect and/or better tolerability.

It is an object of the present invention to provide alternative compositions containing taurine and caffeine, in particular compositions with improved effect and/or better tolerability.

SUMMARY

The present invention therefore provides a pulverulent composition for nasal administration containing taurine, caffeine, L-arginine and L-tryptophan.

Another aspect of the present invention relates to a container containing a pulverulent composition according to the invention. In addition, the invention provides a kit containing a pulverulent composition according to the invention and a nasal applicator (such as a snuffer or a snuff tube). Furthermore, the invention relates to the use of a pulverulent composition, a container, or a kit according to the invention for nasal application of the pulverulent composition.

Furthermore, the invention relates to different uses of pulverulent compositions containing taurine, caffeine, L-arginine and L-tryptophan, inter alia for improving cognitive performance, in particular for increasing the ability to concentrate and/or neural efficiency, for preventing overactivation of brain regions during stress and/or for improving down-regulation after stress, for improving physical performance, in particular for increasing strength and/or endurance, for mood enhancement, for stimulating brain activity, as a flavouring, and/or for enhancing the effect of flavourings, wherein the pulverulent composition is applied nasally, preferably wherein the composition is the pulverulent composition according to the invention.

In conjunction with the present invention, a surprising interaction has been observed, on the one hand, between the individual ingredients of the composition according the to invention, and, on the other hand, between these ingredients and a nasal administration. It was already known from WO 2006/084894 A2 that the administration of tryptophan together with caffeine and taurine can lead to an improvement in cognitive performance. In the context of the present invention, it has now been found, on the one hand, that arginine in combination with taurine and caffeine can also have beneficial effects and, on the other hand, that arginine can interact with the other ingredients and further enhance the effect of tryptophan described in WO 2006/08484 A2. Thus, it has been shown that arginine can enable both an enhancement of the effect at the same dose and a faster onset or longer-lasting effect. Furthermore, it has been shown that nasal administration of the composition, for example as a snuff powder, leads to advantages in terms of strength and course of action as well as in terms of tolerability, particularly in combination with arginine in the composition. The combination of ingredients according to the invention as well as the nasal administration also enable a number of new uses.

The composition according to the invention is preferably a snuff powder, i.e. the composition is preferably suitable for snuffing. Snuff powders are typically finely pulverulent compositions which can be drawn into the nostrils by vigorous intermittent inhalation. Preferably, the composition is suitable for administration to a human, in particular as a snuff powder for a human.

It has been shown that it is advantageous if the particles of the pulverulent composition are not too fine. Without being bound to a specific theory, it is suspected that smaller particles are more likely to reach the lungs during nasal application, while larger particles are absorbed directly through the nasal mucosa and thus the beneficial effects of the invention are better deployed.

It is therefore preferred that the composition has a mean particle size of greater than 1 μm, preferably greater than 5 μm, more preferably greater than 10 μm, even more preferably greater than 20 μm, most preferably greater than 50 μm. In order of increasing preference, it is preferred if the composition has a mean particle size of greater than 1, 2, 3, 4, 5, 6, 7, 8, 9, 10, 11, 12, 13, 14, 15, 16, 17, 18, 19, 20, 25, 30, 35, 40, 45 or 50 μm.

On the other hand, in order to ensure easy aspiration through the nose as well as efficient absorption, it is preferred that the composition has a mean particle size of less than 1,000 μm, preferably less than 500 μm, more preferably less than 200 μm, even more preferably less than 50 μm, most preferably less than 20 μm. It is particularly preferred that the composition has a mean particle size between 1 μm and 1,000 μm, preferably between 5 μm and 500 μm, even more preferably between 20 μm and 200 μm, most preferably between 50 μm and 100 μm.

As used herein, the mean particle size denotes the D50 value of the particle size distribution. The D50 value denotes the value below which 50% of the particle size distribution is found. Similarly, a D10 and D90 value can also be determined as the values below which 10% and 90% of the particle size distribution is located, respectively. The span is a measure of the width of the particle size distribution and can be determined as span=(D90−D10)/D50.

In the context of the present invention, the particle size distribution, in particular the D50, D10, and D90 values, is preferably determined by laser diffraction particle size analysis. In this context, the particle size preferably corresponds to the equivalent diameter of the diffraction-equivalent sphere. The mean particle size preferably corresponds to the volume-based mean particle size, in particular the D50 value of a volumetric particle size distribution. Preferably, the laser diffraction particle size analysis is performed according to the standard ISO 13320:2020. For example, the mean particle size can be determined with the Mastersizer 3000 device from the company Malvern Panalytical.

Alternatively, the mean particle size can also be determined by sieve analysis. A person skilled in the art is familiar with the execution of such an analysis. Preferably, the sieve analysis is carried out according to the German standard DIN 66165-1:2016 08.

In the context of the invention, it is preferred if the proportion of very fine particles is low, among other things because very fine particles can enter the lungs in an increased quantity during nasal application instead of being absorbed via the nasal mucosa. It is therefore preferred that the composition has a particle size distribution with a D10 value of at least 100 nm, preferably at least 500 nm, more preferably at least 1 μm, most preferably at least 2 μm. Preferably, the D10 value is between 100 nm and 50 μm, more preferably between 500 nm and 20 μm, even more preferably between 1 μm and 15 μm, most preferably between 2 μm and 10 μm.

It is further preferred that the pulverulent composition according to the invention has a particle size distribution with a low span ((D90−D10)/D50). In particular, the span is less than 500, preferably less than 100, even more preferably less than 20, most preferably less than 10.

Preferably, the pulverulent composition according to the invention contains at least 1% by weight, preferably at least 2% by weight, more preferably at least 4% by weight, even more preferably at least 8% by weight, even more preferably at least 15% by weight, most preferably at least 20% by weight of taurine. Ranked in order of increasing preference, the composition preferably contains at least 1, 2, 3, 4, 5, 6, 7, 8, 9, 10, 11, 12, 13, 14, 15, 16, 17, 18, 19 or 20% by weight of taurine. It is particularly preferred that the composition contains between 1% by weight and 75% by weight, preferably between 2% by weight and 60% by weight, more preferably between 4% by weight and 50% by weight, even more preferably between 8% by weight and 40% by weight, even more preferably between 15% by weight and 35% by weight, most preferably between 20% by weight and 30% by weight of taurine.

Preferably, the pulverulent composition according to the invention contains at least 0.25% by weight, preferably at least 0.5% by weight, more preferably at least 1% by weight, even more preferably at least 2% by weight, even more preferably at least 4% by weight, most preferably at least 8% by weight of caffeine. Ranked in order of increasing preference, the composition preferably contains at least 0.25, 0.5, 0.75, 1, 1.25, 1.5, 1.75, 2, 2.25, 2.5, 2.75, 3, 3.25, 3.5, 3.75, 4, 4.25, 4.5, 4.75, 5, 5, 25, 5, 75, 6, 6, 25, 6, 5, 6, 75, 7, 7.25, 7.5, 7.75 or 8% by weight of caffeine. It is particularly preferred that the composition contains between 0.25% by weight and 50% by weight, preferably between 0.5% by weight and 35% by weight, more preferably between 1% by weight and 25% by weight, even more preferably between 2% by weight and 20% by weight, even more preferably between 4% by weight and 15% by weight, most preferably between 8% by weight and 12% by weight of caffeine.

Preferably, the pulverulent composition according to the invention contains at least 0.5% by weight, preferably at least 1% by weight, more preferably at least 2% by weight, even more preferably at least 4% by weight, even more preferably at least 8% by weight, most preferably at least 14% by weight of L-arginine. Ranked in order of increasing preference, the composition preferably contains at least 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5 or 14% by weight of L-arginine. It is particularly preferred that the composition contains between 0.5% by weight and 50% by weight, preferably between 1% by weight and 40% by weight, more preferably between 2% by weight and 35% by weight, even more preferably between 4% by weight and 28% by weight, even more preferably between 8% by weight and 22% by weight, most preferably between 14% by weight and 19% by weight of L-arginine.

Preferably, the pulverulent composition according to the invention contains at least 0.25% by weight, preferably at least 0.5% by weight, more preferably at least 1% by weight, even more preferably at least 2% by weight, even more preferably at least 4% by weight, most preferably at least 8% by weight of L-tryptophan. Ranked in order of increasing preference, the composition preferably contains at least 0.25, 0.5, 0.75, 1, 1.25, 1.5, 1.75, 2, 2.25, 2.5, 2.75, 3, 3.25, 3.5, 3.75, 4, 4.25, 4.5, 4.75, 5, 5, 25, 5, 75, 6, 6, 25, 6, 5, 6, 75, 7, 7.25, 7.5, 7.75, 8% by weight of L-tryptophan. It is particularly preferred that the composition contains between 0.25% by weight and 50% by weight, preferably between 0.5% by weight and 35% by weight, more preferably between 1% by weight and 25% by weight, even more preferably between 2% by weight and 20% by weight, even more preferably between 4% and 15% by weight, most preferably between 8% by weight and 12% by weight of L-tryptophan.

In a preferred embodiment, the pulverulent composition according to the invention contains fillers, preferably maltodextrin.

In another preferred embodiment, the composition additionally contains flavouring agents, preferably menthol, vanillin, or fruit flavourings. The possibility of providing different flavouring agents in the composition allows different experiences to be created during use. For example, activating or also calming and soothing flavourings can be selected.

In a further preferred embodiment, the composition additionally contains a fluorescent dye, preferably a fluorescent food dye, in particular riboflavin, tartrazine, yellow orange S, cochineal red A, amaranth, or brilliant blue FCF. Preferably, the fluorescent dye can be excited by UV light, preferably with light of a wavelength between 200 nm and 400 nm, in particular 365 nm. By providing a fluorescent dye, the pulverulent composition is readily visible even in rooms illuminated only with black light (UV light), which makes it particularly easy to use in such environments.

In a particularly preferred embodiment, the composition contains:

between 4% by weight and 40% by weight of taurine;
between 2% by weight and 25% by weight of caffeine;
between 1% by weight and 17% by weight of L-arginine; and
between 1% by weight and 17% by weight of L-tryptophan.

In another particularly preferred embodiment, the composition consists of:

between 4% by weight and 40% by weight of taurine;
between 2% by weight and 25% by weight of caffeine;
between 1% by weight and 17% by weight of L-arginine;
between 1% by weight and 17% by weight of L-tryptophan; and
ad 100% by weight of fillers, in particular maltodextrin.

Since the pulverulent compositions according to the invention are intended for nasal application, it is preferred that certain ingredients which are frequently found in foodstuffs or energy drinks are not present or are present only in low concentrations. Such ingredients may, among other things, irritate the nasal mucosa or lead to other undesirable effects.

It is therefore preferred that the composition according to the invention contains less than 10% by weight, preferably less than 5% by weight, even more preferably less than 1% by weight, even more preferably less than 0.1% by weight, most preferably no sweeteners. Sweeteners as used herein are understood to be sugar substitutes, i.e. food additives intended to provide a sweet taste to food. Sugars, such as maltodextrin, are not sweeteners in the sense of the invention. In a preferred embodiment, the sweeteners are sweetening substances, preferably selected from the group consisting of acesulfame, advantame, aspartame, cyclamate, neotame, sucralose, neohesperidin, saccharin, stevioside and thaumatin. In another preferred embodiment, the sweeteners are sugar substitutes, preferably sugar alcohols, in particular wherein the sugar substitutes are selected from the group consisting of sorbitol, mannitol, isomalt, maltitol, polyglycitol, lactitol, xylitol and erythritol.

Furthermore, it is preferred that the composition contains less than 10% by weight, preferably less than 5% by weight, even more preferably less than 1% by weight, even more preferably less than 0.1% by weight, most preferably no citric acid or citrates. It is further preferred that the composition contains less than 10% by weight, preferably less than 5% by weight, even more preferably less than 1% by weight, even more preferably less than 0.1% by weight, even more preferably less than 0.01% by weight, most preferably no nicotine.

In a further aspect, the invention relates to a container containing the pulverulent composition according to the invention. All described preferred embodiments of the composition according to the invention are also considered preferred embodiments for the container according to the invention.

In a preferred embodiment, the container contains at least 10 mg, preferably at least 50 mg, more preferably at least 200 mg, even more preferably at least 400 mg, most preferably at least 800 mg of the pulverulent composition. Particularly preferably, the container contains between 10 mg and 20,000 mg, more preferably between 50 mg and 10,000 mg, more preferably between 200 mg and 5,000 mg, even more preferably between 400 mg and 2,500 mg, most preferably between 800 mg and 1,250 mg of the pulverulent composition. In the context of the invention, it has been found that this amount is particularly suitable for a single application or for several successive applications. The container thus preferably contains a pre-portioned amount of the composition according to the invention for one application and can be easily disposed of after consumption. This ensures that the user consumes an optimal amount of the composition without having to ensure this amount by weighing or the like.

Any type of container may be used within the scope of the invention. Preferably, it is a sachet, a can, an ampoule, a jar or a bottle. In particular, sachets have proven to be particularly practical, as they can be easily transported and can be easily disposed of after consumption of the composition contained therein.

In another aspect, the invention relates to a kit containing a pulverulent composition according to the invention and a nasal applicator such as a snuffer or a snuff tube. Preferably, the kit contains a container according to the invention and a nasal applicator such as a snuff spoon or a snuff tube. All described preferred embodiments of the composition according to the invention and of the container according to the invention are also considered preferred embodiments for the kit according to the invention.

A snuff tube, often also referred to as a nasal tube or draw tube, is an object that facilitates the nasal consumption of pulverulent compositions. The snuff tube can be placed at the nostril and the composition can be drawn into the nose by vigorous intermittent inhalation through the snuff tube. Preferably, the snuff tube is tubular or channel shaped.

Another nasal applicator is the snuffer—a spoon shaped object which facilitates the nasal application of pulverulent compositions. In addition, the snuffer allows a dose of the pulverulent composition to be removed from the container for nasal application.

In a preferred embodiment, the kit contains at least two, preferably at least three, in particular at least five containers according to the invention. Each of these containers may in turn contain a pre-portioned amount of the composition according to the invention, so that the consumer can consume an optimal amount of the composition for each application without having to weigh it out.

In another aspect, the present invention relates to a use of a pulverulent composition, a container, or a kit according to the invention for nasal application of the pulverulent composition. The application may be carried out, for example, by drawing into the nose the composition distributed on a surface, directly from the container according to the invention (for example from a can), and/or via a nasal applicator such as a snuffer or a snuff tube.

Preferably, the use is for nasal application of the pulverulent composition to a human. The use is therefore preferably by a human being. Preferably, the human is a neurologically and psychiatrically healthy person or a person who has no neurological and/or psychiatric disorders. In particular, the person is a healthy individual.

In a preferred embodiment, the use of the nasal application comprises at least 10 mg, preferably at least 50 mg, more preferably at least 200 mg, even more preferably at least 400 mg, most at least 800 mg of the pulverulent composition. In preferably particular, it is preferred that the use of the nasal application comprises between 10 mg and 5,000 mg, preferably between 50 mg and 4,000 mg, more preferably between 200 mg and 3,000 mg, even more preferably between 400 mg and 2,000 mg, most preferably between 800 mg and 1,250 mg of the pulverulent composition. These amounts have been found to be particularly favourable for a single application, or for several successive applications.

In further aspects, which will be described in greater detail below, the invention relates to a number of different uses of pulverulent compositions, wherein the pulverulent composition is applied nasally. In the context of all the described uses, the pulverulent composition is preferably a pulverulent composition according to the invention as described herein. For all described uses, the container according to the invention or the kit according to the invention (each containing the pulverulent composition according to the invention) may also be used instead of the pulverulent composition. All described preferred embodiments of the composition according to the invention, the container according to the invention, the kit according to the invention and the individual uses according to the invention are also considered preferred embodiments for all uses disclosed herein.

In the uses specified herein, the daily dose of the pulverulent composition is preferably between 10 mg and 20,000 mg, more preferably between 50 mg and 10,000 mg, more preferably between 200 mg and 5,000 mg, even more preferably between 400 mg and 2,500 mg, most preferably between 800 mg and 1,250 mg. This daily dose may be administered in one or more applications, for example in 10 applications with a dose of 100 mg each.

One aspect of the invention relates to the use of a pulverulent composition containing taurine, caffeine, L-arginine and L-tryptophan for improving cognitive performance, in particular for increasing concentration and/or neural efficiency, wherein the pulverulent composition is applied nasally.

Especially with regard to the ability to concentrate, it has been shown that the presence of arginine in the composition leads to a particularly strong effect, including a surprising prolongation of the effect. Furthermore, it has been shown that nasal administration is superior to intake via food, for example as a drink.

The phenomenon of so-called neural efficiency is described for example in Grabner, et al. ("When intelligence loses its impact: Neural efficiency during reasoning in a familiar area." International Journal of Psychophysiology 49.2 (2003): 89-98), Neubauer and Fink ("Intelligence and neural efficiency." Neuroscience & Biobehavioral Reviews 33.7 (2009): 1004-1023) and Dunst, et al ("Neural efficiency as a function of task demands." Intelligence 42 (2014): 22-30). Electron-encephalogram (EEG) imaging techniques have shown that intelligent people are able to limit brain activation to smaller areas of the cerebral cortex, primarily those that are truly necessary for processing the task at hand. Less gifted people, on the other hand, have to activate larger parts of their brain and thus consume more resources for the same task. Neural efficiency is a measure of these psychophysiological differences that occur in the thought processes of intelligent and less intelligent people. The phenomenon of selective activation of areas of the brain that occurs in particularly intelligent people is also called the "genius effect".

It was already known from WO 2006/084894 A1 that the oral administration of tryptophan together with caffeine and taurine can lead to an increase in neural efficiency and to an improvement in cognitive performance. In the context of the present invention, it has been found that, on the one hand, the additional combination with arginine and, on the other hand, a nasal administration enable an improvement of these effects.

After administration of the composition according to the invention, the areas of the brain required for the performance of a specific cognitive and concentrative task are activated in a more targeted manner. In particular, the increase in activity is centred on those areas of the cerebral cortices which are required to cope with a particular cognitive task. Another particular advantage is that the recovery process following stress leads to a more reduced level, i.e. the recovery period is shortened. The composition according to the invention thus leads to the "genius effect", i.e. a brain activity of high neural efficiency, which otherwise only occurs in particularly intelligent people. This effect is even better than the administered known from orally compositions WO 2006/084894 A1 with regard to the strength and course (onset and duration) of the effect.

Another aspect of the invention relates to the use of a pulverulent composition containing taurine, caffeine, L-arginine and L-tryptophan for preventing over-activation of areas of the brain during stress and/or for improving down-regulation after stress, wherein the pulverulent composition is applied nasally. The composition according to the invention can attenuate exaggerated stress responses whilst, however, preserving the hormonal responses necessary to mobilise ergotropic resources. The down-regulation of central nervous activation can be accelerated.

In the context of the invention, it has been shown that the composition according to the invention, in particular due to the presence of L-arginine and the nasal application, has particularly beneficial effects on physical performance. In particular, a strong, rapid-onset and long-lasting effect is made possible. A further aspect of the invention therefore relates to the use of a pulverulent caffeine, L-arginine and composition containing taurine, L-tryptophan for improving physical performance, in particular for increasing strength and/or endurance, wherein the pulverulent composition is applied nasally.

Furthermore, the composition according to the invention can lead to a serotonin release and mood enhancement, as well as to a stimulation of brain activity in a healthy person. Another aspect of the invention therefore relates to the use of a pulverulent composition containing taurine, caffeine, L-arginine and L-tryptophan for mood enhancement, wherein the pulverulent composition is applied nasally. The invention additionally relates to the use of a pulverulent composition containing taurine, caffeine, L-arginine and L-tryptophan for stimulating brain activity, wherein the pulverulent composition is applied nasally.

Surprisingly, it has been shown that the pulverulent composition according to the invention can be used particularly advantageously as a flavouring. After nasal administration, on the one hand the composition itself leads to a positive flavour experience, and on the other hand the composition also acts as a "flavour catalyst" for other flavourings. Thus, after consumption of the composition according to the invention, other flavourings are perceived more intensely. The effect of, for example, a room aroma or another administered aroma/flavouring is thereby enhanced. Without being bound to a specific theory, it is suspected that the nasal application enables a direct effect of the composition on the olfactory epithelium in the nasal cavity.

Another aspect of the invention therefore relates to the use of a pulverulent composition containing taurine, caffeine, L-arginine and L-tryptophan as a flavouring, wherein the pulverulent composition is applied nasally.

The invention therefore further relates to the use of a pulverulent composition containing taurine, caffeine, L-arginine and L-tryptophan for enhancing the effect of flavourings, wherein the pulverulent composition is applied nasally. The use preferably comprises the administration of at least one further flavouring. The further flavouring may also be applied nasally, for example as a powder, as a liquid, or as an aerosol, or may also be administered via the room air, for example via a diffuser or a scented candle. The further flavouring is preferably a synthetic or natural flavouring agent, for example vanillin or menthol, or a flavour extract, in particular from fruits, spices, or herbs, or an essential oil. Advantageously, the use can also take place before the ingestion of food and/or beverages, for example in restaurants or bars, whereby the taste experience is intensified.

DETAILED DESCRIPTION

All parameters mentioned herein, unless otherwise indicated, refer to SATP conditions according to IUPAC ("Standard Ambient Temperature and Pressure"), in particular to a temperature of 25° C. and a pressure of 101,300 Pa. All percentages (%) herein are by weight unless otherwise indicated. All references to ingredients in the disclosed compositions, in particular taurine, caffeine, L-arginine and L-tryptophan, include compatible salts thereof.

In particular, the present invention discloses the following preferred embodiments:

- Embodiment 1: A pulverulent composition for nasal application containing taurine, caffeine, L-arginine and L-tryptophan.
- Embodiment 2: The pulverulent composition according to embodiment 1, characterized in that the composition has a mean particle size of more than 1 μm, preferably more than 5 μm, more preferably more than 10 μm, even more preferably more than 20 μm, most preferably more than 50 μm.
- Embodiment 3: The pulverulent composition according to embodiment 1 or 2, characterized in that the composition has a mean particle size of less than 1,000 μm, preferably less than 500 μm, more preferably less than 200 μm, even more preferably less than 50 μm, most preferably less than 20 μm.
- Embodiment 4: The pulverulent composition according to any one of embodiments 1 to 3, characterized in that the composition has a mean particle size between 1 μm and 1,000 μm, preferably between 5 μm and 500 μm, even more preferably between 20 μm and 200 μm, most preferably between 50 μm and 100 μm.
- Embodiment 5: The pulverulent composition according to any one of embodiments 1 to 4, characterized in that the composition contains at least 1% by weight, preferably at least 2% by weight, more preferably at least 4% by weight, even more preferably at least 8% by weight, even more preferably at least 15% by weight, most preferably at least 20% by weight of taurine.
- Embodiment 6: The pulverulent composition according to any one of embodiments 1 to 5, characterized in that the composition contains between 1% by weight and 75% by weight, preferably between 2% by weight and 60% by weight, more preferably between 4% by weight and 50% by weight, even more preferably between 8% by weight and 40% by weight, even more preferably between 15% by weight and 35% by weight, most preferably between 20% by weight and 30% by weight of taurine.
- Embodiment 7: The pulverulent composition according to any one of embodiments 1 to 6, characterized in that the composition contains at least 0.25% by weight, preferably at least 0.5% by weight, more preferably at least 1% by weight, even more preferably at least 2% by weight, even more preferably at least 4% by weight, most preferably at least 8% by weight of caffeine.
- Embodiment 8: A pulverulent composition according to any one of embodiments 1 to 7, characterized in that the composition contains between 0.25% by weight and 50% by weight, preferably between 0.5% by weight and 35% by weight, more preferably between 1% by weight and 25% by weight, even more preferably between 2% by weight and 20% by weight, even more preferably between 4% by weight and 15% by weight, most preferably between 8% by weight and 12% by weight of caffeine.
- Embodiment 9: The pulverulent composition according to any one of embodiments 1 to 8, characterized in that the composition contains at least 0.5% by weight, preferably at least 1% by weight, more preferably at least 2% by weight, even more preferably at least 4% by weight, even more preferably at least 8% by weight, most preferably at least 14% by weight of L-arginine.
- Embodiment 10: The pulverulent composition according to any one of embodiments 1 to 9, characterized in that the composition contains between 0.5% by weight and 50% by weight, preferably between 1% by weight and 40% by weight, more preferably between 2% by weight and 35% by weight, even more preferably between 4% by weight and 28% by weight, even more preferably between 8% by weight and 22% by weight, most preferably between 14% by weight and 19% by weight of L-arginine.
- Embodiment 11: The pulverulent composition according to any one of embodiments 1 to 10, characterized in that the composition contains at least 0.25% by weight, preferably at least 0.5% by weight, more preferably at least 1% by weight, even more preferably at least 2% by weight, even more preferably at least 4% by weight, most preferably at least 8% by weight of L-tryptophan.
- Embodiment 12: The pulverulent composition according to any one of embodiments 1 to 11, characterized in that the composition contains between 0.25% by weight and 50% by weight, preferably between 0.5% by weight and 35% by weight, more preferably between 1% by weight and 25% by weight, even more preferably between 2% by weight and 20% by weight, even more preferably between 4% by weight and 15% by weight, most preferably between 8% by weight and 12% by weight of L-tryptophan.
- Embodiment 13: The pulverulent composition according to any of embodiments 1 to 12, characterised in that the composition additionally contains fillers, preferably maltodextrin.
- Embodiment 14: The pulverulent composition according to any of embodiments 1 to 13, characterised in that the composition additionally contains flavouring agents, preferably menthol, vanillin, or fruit flavourings.
- Embodiment 15: Pulverulent composition according to any one of embodiments 1 to 14, characterized in that the composition additionally contains a fluorescent dye, preferably a fluorescent food dye, in particular riboflavin, tartrazine, yellow orange S, cochineal red A, amaranth, or brilliant blue FCF.
- Embodiment 16: A pulverulent composition according to any one of embodiments 1 to 15, characterized in that the composition contains:
  - between 4% by weight and 40% by weight of taurine;
  - between 2% by weight and 25% by weight of caffeine;
  - between 1% by weight and 17% by weight of L-arginine; and
  - between 1% by weight and 17% by weight of L-tryptophan.

Embodiment 17: Pulverulent composition according to any one of embodiments 1 to 13, characterized in that the composition consists of:

between 4% by weight and 40% by weight of taurine;
between 2% by weight and 25% by weight of caffeine;
between 1% by weight and 17% by weight of L-arginine;
between 1% by weight and 17% by weight of L-tryptophan; and
ad 100% by weight of fillers.

Embodiment 18: The pulverulent composition according to any one of embodiments 1 to 17, characterized in that the composition contains less than 10% by weight, preferably less than 5% by weight, even more preferably less than 1% by weight, even more preferably less than 0.1% by weight, most preferably no sweeteners.

Embodiment 19: The pulverulent composition according to embodiment 18, characterized in that the sweeteners are sweetening substances, preferably selected from the group consisting of acesulfame, advantame, aspartame, cyclamate, neohesperidin, neotame, saccharin, sucralose, stevioside and thaumatin.

Embodiment 20: The pulverulent composition according to embodiment 18, characterized in that the sweeteners are sugar substitutes, preferably sugar alcohols, in particular wherein the sugar substitutes are selected from the group consisting of sorbitol, mannitol, isomalt, maltitol, polyglycitol, lactitol, xylitol and erythritol.

Embodiment 21: The pulverulent composition according to any one of embodiments 1 to 20, characterized in that the composition contains less than 10% by weight, preferably less than 5% by weight, even more preferably less than 1% by weight, even more preferably less than 0.1% by weight, most preferably no citric acid or citrates.

Embodiment 22: The pulverulent composition according to any one of embodiments 1 to 21, characterized in that the composition contains less than 10% by weight, preferably less than 5% by weight, even more preferably less than 1% by weight, even more preferably less than 0.1% by weight, even more preferably less than 0.01% by weight, most preferably no nicotine.

Embodiment 23: A container containing a pulverulent composition according to any one of embodiments 1 to 22.

Embodiment 24: The container according to embodiment 23, characterized in that the container contains at least 10 mg, preferably at least 50 mg, more preferably at least 200 mg, even more preferably at least 400 mg, most preferably at least 800 mg of the pulverulent composition.

Embodiment 25: The container according to embodiment 23 or 24, characterized in that the container contains between 10 mg and 20,000 mg, preferably between 50 mg and 10,000 mg, more preferably between 200 mg and 5,000 mg, even more preferably between 400 mg and 2,500 mg, most preferably between 800 mg and 1,250 mg of the pulverulent composition.

Embodiment 26: The container according to any one of embodiments 23 to 25, characterized in that the container is a sachet, a can, an ampoule, a jar or a bottle.

Embodiment 27: A kit containing a pulverulent composition according to any one of embodiments 1 to 22 and a nasal applicator such as a snuffer or a snuff tube.

Embodiment 28: The kit according to embodiment 27, characterised in that the kit contains a container according to any one of embodiments 23 to 26.

Embodiment 29: The kit according to embodiment 27 or 28, characterised in that the kit contains at least two, preferably at least three, in particular at least five containers according to one of embodiments 23 to 26.

Embodiment 30: Use of a pulverulent composition according to any one of embodiments 1 to 22, a container according to any one of embodiments 23 to 26, or a kit according to any one of embodiments 27 to 29 for nasal application of the pulverulent composition.

Embodiment 31: The use according to embodiment 30, characterized in that the use comprises nasal application of at least 10 mg, preferably at least 50 mg, more preferably at least 200 mg, even more preferably at least 400 mg, most preferably at least 800 mg of the pulverulent composition.

Embodiment 32: The use according to embodiment 30 or 31, characterized in that the use comprises nasal application of between 10 mg and 5,000 mg, preferably between 50 mg and 4,000 mg, more preferably between 200 mg and 3,000 mg, even more preferably between 400 mg and 2,000 mg, most preferably between 800 mg and 1, 250 mg of the pulverulent composition.

Embodiment 33: Use of a pulverulent composition containing taurine, caffeine, L-arginine and L-tryptophan for improving cognitive performance, in particular for enhancing concentration and/or neural efficiency, wherein the pulverulent composition is applied nasally, preferably wherein the composition is as defined in any one of embodiments 2 to 22.

Embodiment 34: Use of a pulverulent composition containing taurine, caffeine, L-arginine and L-tryptophan for preventing overactivation of areas of the brain during stress and/or for improving down-regulation after stress, wherein the pulverulent composition is applied nasally, preferably wherein the composition is as defined in any one of embodiments 2 to 22.

Embodiment 35: Use of a pulverulent composition containing taurine, caffeine, L-arginine and L-tryptophan for improving physical performance, in particular for increasing strength and/or endurance, wherein the pulverulent composition is applied nasally, preferably wherein the composition is as defined in any one of embodiments 2 to 22.

Embodiment 36: Use of a pulverulent composition containing taurine, caffeine, L-arginine and L-tryptophan for mood elevation, wherein the pulverulent composition is applied nasally, preferably wherein the composition is as defined in any one of embodiments 2 to 22.

Embodiment 37: Use of a pulverulent composition containing taurine, caffeine, L-arginine and L-tryptophan for stimulating brain activity, wherein the pulverulent composition is applied nasally, preferably wherein the composition is as defined in any one of embodiments 2 to 22.

Embodiment 38: Use of a pulverulent composition containing taurine, caffeine, L-arginine and L-tryptophan as a flavouring, wherein the pulverulent composition is applied nasally, preferably wherein the composition is as defined in any one of embodiments 2 to 22.

Embodiment 39: Use of a pulverulent composition containing taurine, caffeine, L-arginine and L-tryptophan for enhancing the effect of flavourings, wherein the pulverulent composition is applied nasally, preferably wherein the composition is as defined in any one of embodiments 2 to 22.

Embodiment 40: Use according to any one of embodiments 30 to 39, wherein the daily dose of the pulverulent composition is between 10 mg and 20,000 mg, preferably between 50 mg and 10,000 mg, more preferably between 200 mg and 5,000 mg, even more preferably between 400 mg and 2,500 mg, most preferably between 800 mg and 1,250 mg.

The invention will also be explained in greater detail with reference to the following example, to which it is of course not limited.

Example 1 kg of the pulverulent composition is obtained by mixing the following ingredients (in powder form): 250 g of taurine, 150 g of L-arginine HCl, 100 g of caffeine anhydrate, 100 g of L-tryptophan and 400 g of maltodextrin. The mean particle size of the composition is 75 μm. The composition is packaged in sachets of 1 gram each.

By means of a snuffer, 5×200 mg (i.e. the total content of one sachet) are administered to an adult human test subject throughout the day.

The invention claimed is:

1. A method of using a pulverulent composition containing taurine, caffeine, L arginine and L tryptophan, comprising administering the composition to a human individual, wherein the composition contains:
- between 4% by weight and 40% by weight of taurine;
- between 2% by weight and 25% by weight of caffeine;
- between 1% by weight and 17% by weight of L-arginine; and
- between 1% by weight and 17% by weight of L-tryptophan.

2. The method of claim 1, wherein the composition has a mean particle size of more than 1 μm.

3. The method of claim 1, wherein the composition is administered via a nasal applicator.

4. The method of claim 1, wherein the nasal applicator is a snuffer or a snuff tube.

* * * * *